(12) United States Patent
MacDougald et al.

(10) Patent No.: US 7,135,611 B2
(45) Date of Patent: Nov. 14, 2006

(54) COMPOSITIONS AND METHODS FOR CHARACTERIZING AND REGULATING WNT PATHWAYS

(75) Inventors: Ormond A. MacDougald, Ypsilanti, MI (US); Kenneth A. Longo, Ann Arbor, MI (US); Sarah E. Ross, Brighton, MA (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/755,594

(22) Filed: Jan. 12, 2004

(65) Prior Publication Data

US 2004/0216176 A1 Oct. 28, 2004

Related U.S. Application Data

(60) Provisional application No. 60/439,386, filed on Jan. 10, 2003.

(51) Int. Cl.
*A01K 67/027* (2006.01)
*A01K 67/033* (2006.01)
*A01K 67/00* (2006.01)
*C07H 21/02* (2006.01)
*C07H 21/04* (2006.01)

(52) U.S. Cl. ............... 800/18; 800/8; 800/13; 800/14; 536/23.1

(58) Field of Classification Search ............ 800/8, 800/13, 14, 18; 536/23.1
See application file for complete search history.

(56) References Cited

OTHER PUBLICATIONS

Cameron (1997, Molecular Biotechnology, 7: 253-265).*
Mench (1999, Transgenic Animals in Agriculture, eds. Murray et al., CAB International: Oxon, pp. 251-268).*
Hammer et al (1990, Cell, 63: 1099-1112).*
Cowan et al. (2003, Xenotransplantation, 10: 223-231).*
Taylor-Jones et al. (2002, Mech Ageing Dev., 123: 649-661).*
Watson et al. (1993, "The introduction of Foreign Genes into Mice," Molecular Biology of Watson Recombinant DNAs, 2nd Edition, p. 255-272).*
Cheneval et al. (1991, PNAS, USA, 88: 8465-8469).*
Longo et al., 2002, Developmental Biology, 247: 517.*
Fukumoto et al., J. Biol. Chem. 276:17479 [2001].
Lane et al., Oncogene 15:2133 [1997].
Ross et al., Science 289:950 [2000].
Buckingham, Curr. Opin. Genet. Dev. 11:440 [2001].
Nusse et al., Cell 69:1073 [1992].
Miller et al., Oncogene 18:7860 [1999].
Tamai et al., Nature 407:530 [2000].
Kuhl et al., Trends Genet. 16(7):279-83 [2000].
Bennett et al., J. Biol. Chem. 277:30998 [2002].
Macdougald et al., Trends Endocrinol. Metab. 13:5 [2002].
Bournat et al., J. Neurosci. Res. 61:21 [2000].
Chen et al., J. Cell. Biol. 152:87 [2001].
Longo et al., JBC 277: 38239-38244 [2002].
Wolff, J. Natr. 127:1897S [1997].
Kato et al., J Cell Biol 2002, 157:303-14.
Longo et al., Developmental Biology 247:517 (2002) (Abstract only).
McDougald, Intl J. of Obesity 26:S212 (2002) (Abstract only).
Christiansen et al., Mechanisms of Development 51:341-350 (1995).
Wang et al., Oncogene 13:1537-1544 (1996).
Lee et al., Proceedings of the Natl Academy of Sciences of the USA 92:2268-2272 (1995).
Brockman et al., Trends in Genetics 18:367-376 (2002).

* cited by examiner

*Primary Examiner*—Anne M. Wehbe
*Assistant Examiner*—Joanne Hama
(74) *Attorney, Agent, or Firm*—Medlen & Carroll, LLP

(57) ABSTRACT

The present invention relates to transgenic animal models for altered Wnt expression. The present invention also provides methods for generating animal models and screening methods for identifying biologically active compounds.

3 Claims, 14 Drawing Sheets

Figure 4
Femoral distal metaphyseal trabecular analysis
| | Transgenic | Wildtype |
|---|---|---|
| Bone volume fraction (%)* | 15.75 (4.02) | 3.73 (1.20) |
| Bone surface (ratio to bone volume) * | 63.62 (11.51) | 88.52 (13.90) |
| Trabecular Thickness (mm)* | 0.033 (0.005) | 0.024 (0.004) |
| Trabecular Number* | 4.71 (0.55) | 1.43 (0.58) |
| Trabecular Spacing (mm)* | 0.188 (0.035) | 0.950 (0.360) |
| Trabecular BMD (mg/cc) | 1887.4 (499.5) | 3183.0 (2061.2) |
1. Based on the analysis of a 1 mm$^3$ cube in the distal metaphysis
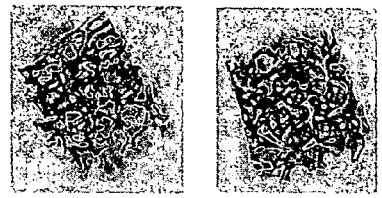

Wnt10b blocks expression of adipocyte genes in adult mice

*Wnt10b transgenic mice unresponsive to β3-agonist

Effect of Wnt10b on Expression of Adipocyte Genes

Main phenotype: Decreased mass of WAT

Respiratory quotient in control and Wnt10b transgenic mice

Conclusion: Wnt10b transgenic mice do not store, mobilize and metabolize fat as dynamically as wild type littermates Wnt10b transgenic mice are more sensitive to insulin

COMPOSITIONS AND METHODS FOR CHARACTERIZING AND REGULATING WNT PATHWAYS

This Application claims priority to provisional patent application serial No. 60/439,386, filed Jan. 10, 2003, which is herein incorporated by reference in its entirety.

This invention was made with government support under Grant No. DK 51563 awarded by the National Institutes of Health. The Government has certain rights in the invention.

FIELD OF THE INVENTION

The present invention relates to transgenic animal models for altered Wnt expression. The present invention also provides methods for generating animal models and screening methods for identifying biologically active compounds.

BACKGROUND

Obesity and obesity related diseases are a significant health problem. Obesity is an excess proportion of total body fat. A person is considered obese when his or her weight is 20% or more above normal weight. About 39 million Americans currently fall into that category—an all-time high as of 2002. The cost of treating obesity and obesity-related diseases in America accounts for $238 billion, or approximately 20% of the nation's total health care bill, according to the American Obesity Association.

Substantial excess body fat may cause serious health problems. Extra pounds put great strain on the cardiovascular system, contributing to high blood pressure and heart disease, while high fat concentrations can enlarge the liver. Obesity also increases the risk of colorectal cancer.

An additional obesity related illness is adult onset, or Type 2 diabetes. Excessive weight gain may trigger Type 2 diabetes, in which body tissues become resistant to insulin produced by the pancreas. About 80 percent of people with Type 2 diabetes are obese. As a consequence of its microvascular pathology, diabetes is a leading cause of blindness, end-stage renal disease and a variety of debilitating neuropathies. Diabetes is also associated with accelerated atherosclerotic macrovascular disease affecting arteries that supply the heart, brain and lower extremities. As a result, patients with diabetes have a much higher risk of myocardial infarction, stroke and limb amputation.

The exact cause of obesity is still unknown. In addition, the exact causal link between obesity and obesity related illnesses are unknown. Research aimed at determining the cause of obesity and the link with related illnesses has been unsuccessful.

What is needed is a better understanding of the molecular biology and genetics surrounding obesity. In addition, what is needed are better empirical models from which to study obesity and its related illnesses.

SUMMARY OF THE INVENTION

The present invention relates to transgenic animal models for altered Wnt expression. The present invention also provides methods for generating animal models and screening methods for identifying biologically active compounds.

For example, in some embodiments, the present invention provides a transgenic animal whose genome comprises a heterologous gene that alters the expression of Wnt10b in said animal, wherein the animal exhibits decreased fat accumulation. In some embodiments, the heterologous gene overexpresses said Wnt10b. In some embodiments, the transgenic animal is a rodent (e.g., a mouse or a rat). In other embodiments, the transgenic said animal is a livestock animal (e.g., including, but not limited to, a cow, a sheep, or a pig). In some embodiments, the fat is subcutaneous fat. In some embodiments, the fat is white adipose tissue. In other embodiments, the fat is brown adipose tissue.

The present invention also provides a transgenic animal whose genome comprises a heterologous gene that alters the expression of Wnt10b in said animal, wherein the animal exhibits an altered phenotype comprising increased glucose tolerance, increased insulin sensitivity, increased cold sensitivity, increased muscle mass, increased bone density, decreased subcutaneous fat, elevated subcutaneous collagen, increased subcutaneous mast cells, or altered expression of genes in adipose tissue or muscle. In some embodiments, the heterologous gene overexpresses Wnt10b. In some embodiments, the transgenic animal is a rodent (e.g., a mouse or a rat). In other embodiments, the transgenic said animal is a livestock animal (e.g., including, but not limited to, a cow, a sheep, or a pig). In some embodiments, the transgenic animal exhibits two or more of the altered phenotypes.

The present invention further provides a transgenic animal whose genome comprises a heterologous gene that alters the expression of Wnt10b in the animal, wherein said animal exhibits an altered phenotype comprising increased fat accumulation, decreased glucose tolerance, decreased insulin sensitivity, decreased muscle mass, decreased cold sensitivity, decreased bone density, increased subcutaneous fat, decreased subcutaneous collagen, decreased subcutaneous mast cells or altered expression of genes in adipose tissue or muscle. In some embodiments, the heterologous gene is a Wnt10b null. In some embodiments, the transgenic animal is a rodent (e.g., a mouse or a rat). In other embodiments, the transgenic said animal is a livestock animal (e.g., including, but not limited to, a cow, a sheep, or a pig). In some embodiments, the fat is subcutaneous fat. In some embodiments, the fat is white adipose tissue. In other embodiments, the fat is brown adipose tissue.

The present invention additionally provides a method of identifying compounds, comprising exposing a transgenic animal whose genome comprises a heterologous gene that alters the expression of Wnt10b in said animal, wherein the animal exhibits increased or decreased fat accumulation, to one or more test compounds; and detecting a change in the fat accumulation in the presence of the test compound (e.g., compared to an animal not given the test compound). In some embodiments, the test compound is a drug candidate. In some embodiments, the heterologous gene overexpresses said Wnt10b. In some embodiments, the transgenic animal is a rodent (e.g., a mouse or a rat). In other embodiments, the transgenic said animal is a livestock animal (e.g., including, but not limited to, a cow, a sheep, or a pig).

In still further embodiments, the present invention additionally provides a method of identifying compounds, comprising exposing a transgenic animal whose genome comprises a heterologous gene that alters the expression of Wnt10b in said animal, wherein the animal exhibits an altered phenotype comprising increased glucose tolerance, increased insulin sensitivity, increased bone density, increased muscle mass, altered expression of genes in adipose tissue or muscle, or increased cold sensitivity, to a plurality of test compounds; and detecting a change in the altered phenotype in the presence of the test compound. In some embodiments, the test compound is a drug candidate. In some embodiments, the heterologous gene overexpresses said Wnt10b.

In yet other embodiments, the present invention additionally provides a method of identifying compounds, comprising exposing a transgenic animal whose genome comprises a heterologous gene that alters the expression of Wnt10b in said animal, wherein the animal exhibits an altered phenotype comprising increased fat accumulation, decreased glucose tolerance, decreased insulin sensitivity, decreased bone density, decreased muscle mass, altered expression of genes in adipose tissue or muscle, or decreased cold sensitivity, to a plurality of test compounds; and detecting a change in the altered phenotype in the presence of the test compound. In some embodiments, the test compound is a drug candidate. In some embodiments, the heterologous gene is a Wnt10b null.

DESCRIPTION OF THE DRAWINGS

FIG. 4 shows femoral distal metaphyseal trabecular analysis of Wnt10b transgenic mice.

DEFINITIONS

Figure 1:
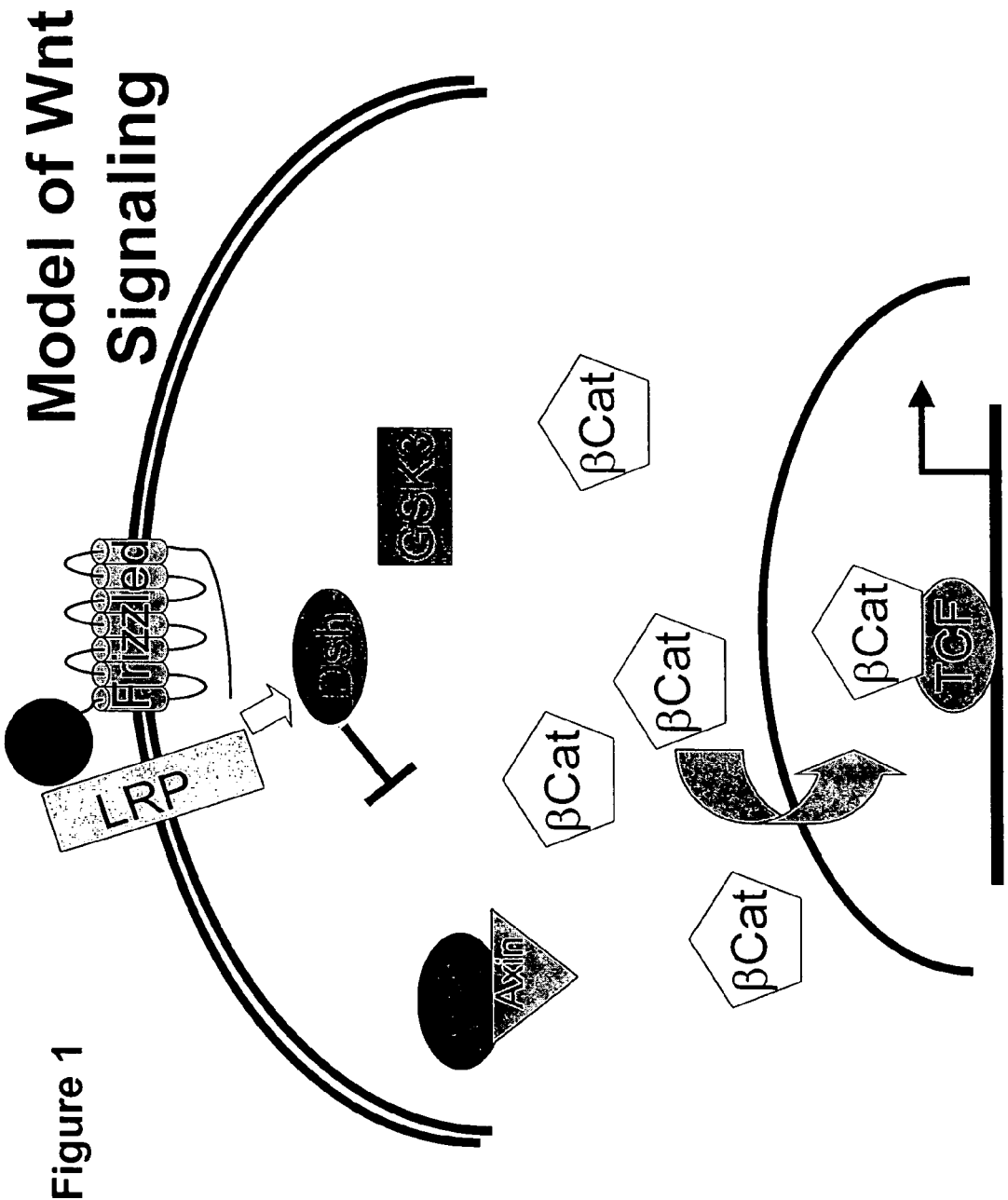
FIG. 1 shows a model of Wnt signaling.

To facilitate an understanding of the invention, a number of terms are defined below.

As used herein, the term "animal" refers to any animal (e.g., a mammal), including, but not limited to, humans, non-human primates, rodents (e.g., mice, rats, etc.), flies, and the like.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene disruption" refers to any heritable genetic alteration that prevents normal production of a protein (e.g., prevents expression of a Wnt10b gene product, expression of normal Wnt10b gene product, or prevents expression of normal amounts of the Wnt10b gene product). In some embodiments, the gene disruption comprises a deletion of all or a portion of the Wnt10b gene. In other embodiments, the gene disruption comprises an insertion or other mutation of the Wnt10b gene. In still other embodiments, the gene disruption is a genetic alteration that prevents expression, processing, or translation of the Wnt10b gene. In one embodiment, both Wnt10b gene alleles are functionally disrupted such that expression of the Wnt10b gene product is substantially reduced or absent in cells of the animal. The term "substantially reduced or absent" is intended to mean that essentially undetectable amounts of normal Wnt10b gene product are produced in cells of the animal. This type of mutation is also referred to as a "null mutation" and an animal carrying such a null mutation is also referred to as a "knockout animal."

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (including heteronuclear RNA; hnRNA and mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region can comprise of cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. Coding regions in eukaryotes are a composition comprising of 5' ends with nucleotide triplets "ATG" that encode methionine and 3' end sequences comprising of nucleotide triplets that specify stop codons (e.g., TAA, TAG, TGA).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "transgenic animal" refers to any animal containing a transgene.

As used herein, the term "vector" is used in reference to nucleic acid molecules that transfer DNA segment(s) from one cell to another. Vector can include partial genes, gene fragments, full length genes and target sequences. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells utilize promoters, enhancers, and termination and polyadenylation signals.

As used herein, the term host cell refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression greater (e.g., approximately 2-fold or more higher) than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, often referred to as "housekeeping" genes (e.g., the amount of 28S rRNA, an abundant RNA transcript present at essentially the same amount in all tissues, present in each sample can be used as a means of normalizing or standardizing the mRNA-specific signal observed on Northern blots).

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has integrated foreign DNA into its genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for up to several cell divisions. During this time the foreign DNA is subject to the regulatory controls that govern the expression of endogenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise cell lysate, a cell, a portion of a tissue, tissue lysate and the like.

DETAILED DESCRIPTION OF THE INVENTION

The present invention provides transgenic animals having somatic and germ cells in which endogenous or exogenous wnt10b gene expression is altered (e.g., increased or decreased). Preferred embodiments of the present invention are illustrated below using the example of a wnt10b overexpressing mouse model. In other embodiments, the mouse may be heterozygous or, more preferably, homozygous for a wnt10b gene disruption. Such animals find use in a variety of applications, including, but not limited to, those described below.

I. Wnt Signaling

The Wnts are a family of 18 secreted proteins that act locally to affect cell fate and differentiation, including adipogenesis, myogenesis, neurogenesis, and mammary development (Fukumoto et al., J. Biol. Chem. 276:17479 [2001]; Lane et al., Oncogene 15:2133 [1997]; Ross et al., Science 289:950 [2000]; Buckingham, Curr. Opin. Genet. Dev. 11:440 [2001]). The Wnt-1 gene was first identified as an insertion site for mouse mammary tumor virus in mouse mammary carcinoma (Nusse et al., Cell 69:1073 [1992]).

Wnts are secreted glycoproteins that interact with seven transmembrane frizzled receptors and low density lipoprotein receptor-related protein co-receptors (Miller et al., Oncogene 18:7860 [1999]; Tamai et al., Nature 407:530 [2000]). In the canonical Wnt signaling pathway, inhibition of GSK-3 prevents phosphorylation and targeted degradation of β-catenin. In the absence of Wnt signaling, hypophosphorylated β-catenin accumulates in the cytoplasm, enters the nucleus, and activates TCF/LEF-dependent gene transcription (Kuhl et al., Trends Genet. 1279 [2000]).

Both Wnt-1 and Wnt-10b block adipogenic conversion of 3T3-L1 preadipocytes through stabilization of β-catenin and inhibition of C/EBPα and peroxisome proliferator-activated receptor γ expression (Ross et al., supra). FIG. 1 shows a diagram of a model of Wnt signaling. Inhibition of Wnt signaling with dominant negative TCF-4 or with soluble frizzled-related proteins (sFRP) causes spontaneous differentiation (Ross et al., supra), indicating that an endogenous Wnt feeds back to repress adipogenesis. Wnt-10b is the best candidate for the endogenous inhibitor because Wnt-10b stabilizes free cytosolic β-catenin, inhibits adipogenesis, and is expressed in preadipocytes and stromovascular cells but not in adipocytes (Ross et al., supra; Bennett et al., J. Biol. Chem. 277:30998 [2002]). Wnt10b is expression in preadipocytes and SV. Suppression of Wnt-10b in response to elevated cAMP promotes expression of adipogenic transcription factors and proteins involved in carbohydrate and lipid metabolism (Macdougald et al., Trends Endocrinol. Metab. 13:5 [2002]).

In addition to playing a key role in adipogenesis, Wnt signaling protects against apoptosis in cells exposed to cellular or chemical stress (Boumat et al., J. Neurosci. Res. 61:21 [2000]). For example, ectopic expression of Wnt-1 in Rat-1 cells inhibits apoptosis in response to vincristine or vinblastine through a PKB/Akt-independent mechanism (Chen et al., J. Cell. Biol. 152:87 [2001]). Furthermore, low serum conditions fail to induce apoptosis in preadipocytes or PC-12 cells that express Wnt-1 (Longo et al., JBC 277: 38239–38244; Boumat et al., supra). Inhibitors of GSK-3 and P13K each partially reversed this effect, suggesting that the cytoprotective effects of Wnt-1 are mediated through direct Wnt signaling and Wnt-induced gene expression. Consistent with an indirect mechanism, recent microarray data demonstrates that Wnt-1 induces expression of a number of antiapoptotic genes, including insulin-like growth factor 1 (Longo et al., JBC 277: 38239–38244 [2002]).

II. Wnt10b Transgenic Animals

Figure 3:
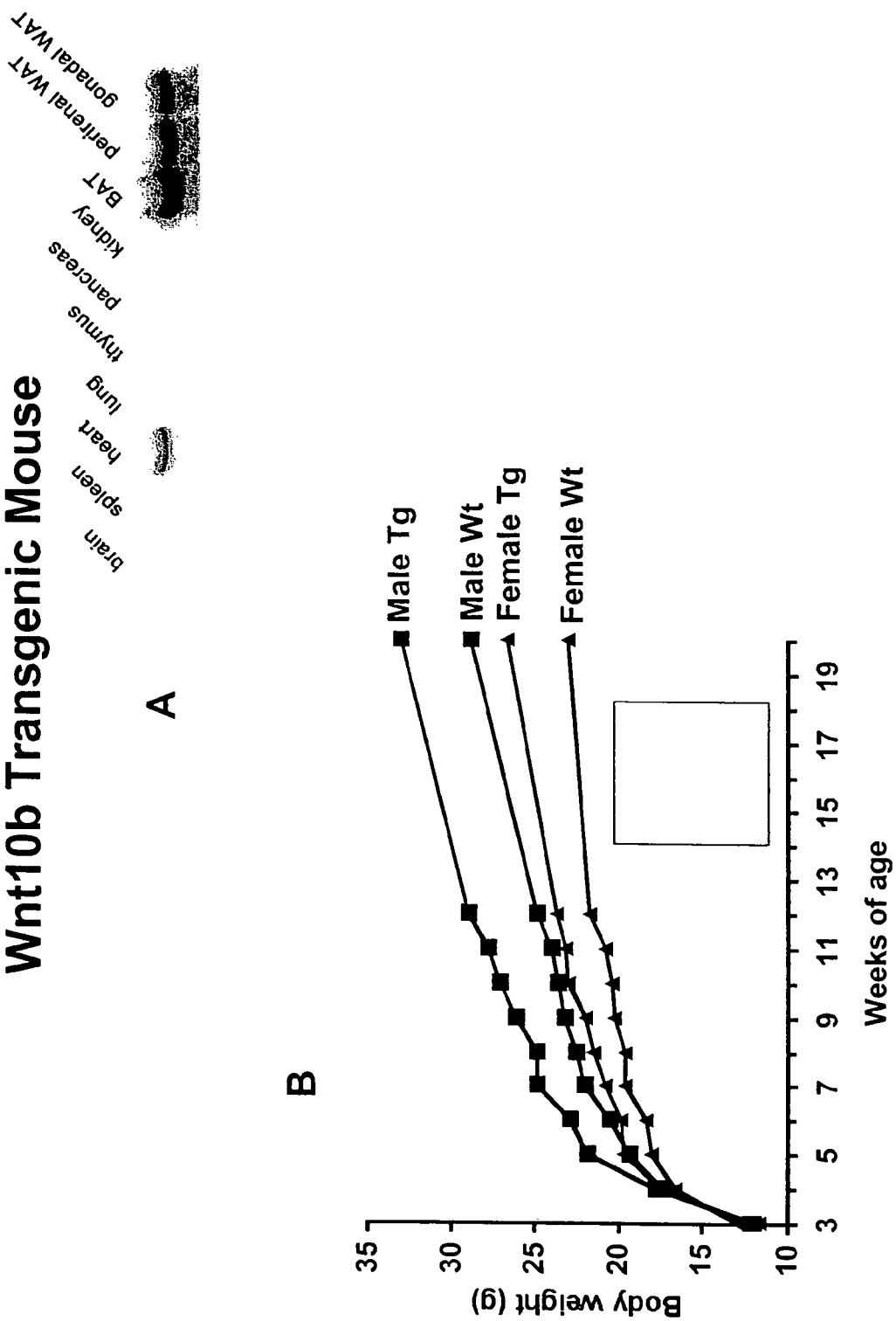
FIG. 3 shows expression of the Wnt transgene in WAT and BAT (FIG. 3A) and weight of transgenic animals (FIG. 3B).
Figure 5:
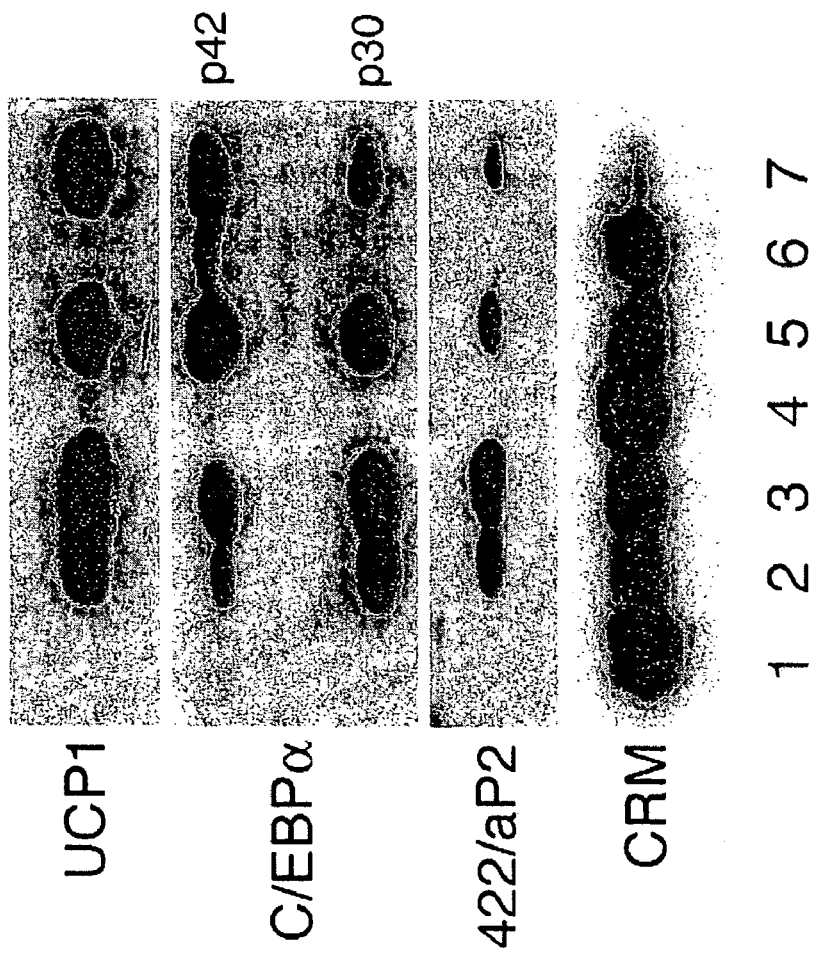
FIG. 5 shows that Wnt10b blocks expression of adipocyte genes in newborn mice.
Figure 6:
FIG. 6 shows that Wnt10b blocks expression of adipocyte genes in adult mice.
Figure 7:
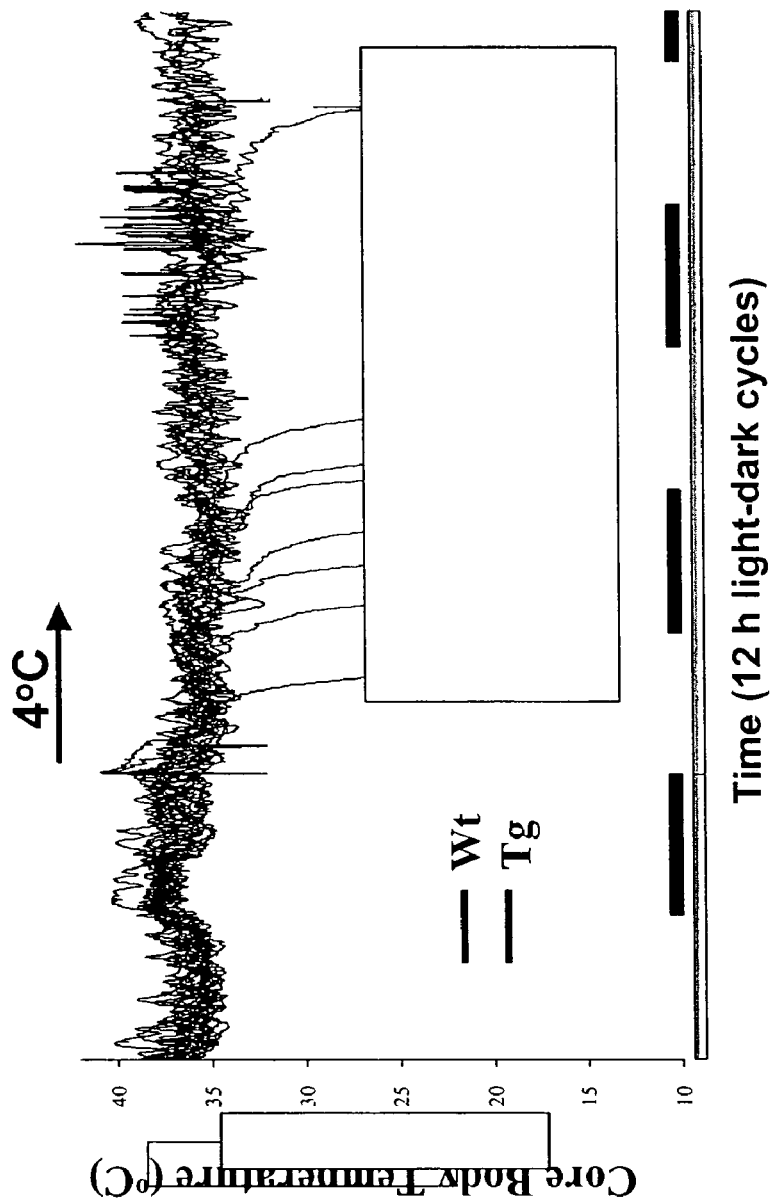
FIG. 7 shows that Wnt10b transgenic mice are cold-sensitive.

In experiments conducted during the course of development of the present invention, a Wnt10b overexpressing transgenic mouse was generated with the Wnt10b gene under the control of the 7.6 kb of the 422/aP2 promoter (See Example 1). Eight founders were generated; three of which exhibited the Wnt overexpression phenotype. Females were fertile but do not nurse, thus lines were carried through males. The transgene was expressed in both white adipose tissue (WAT) and brown adipose tissue (BAT) (FIG. 3). The transgenics were lighter in weight at 3 weeks of age but heavier at 5 weeks of age. The transgenic mice exhibited altered bone trabecular thickness and spacing (FIG. 4). The transgenic mice showed inhibition of brown adipose tissue development 72 hours after birth, as demonstrated by microscopy of tissue cross sections. The transgenic mice also exhibited reduced WAT, with an ovarian fat pad of 15% of the wild type mice and a perirenal fat pad of 25% of the wild type mice. FIG. 5 demonstrates that Wnt10b overexpression in the transgenics blocks expression of adipocytes genes in newborn mice and adult mice (FIG. 6). The transgenic mice were also found to be cold sensitive (FIG. 7). The transgenic mice were further found to exhibit decreased levels of subcutaneous fat, elevated subcutaneous collagen and increased mast cells.

Figure 8:
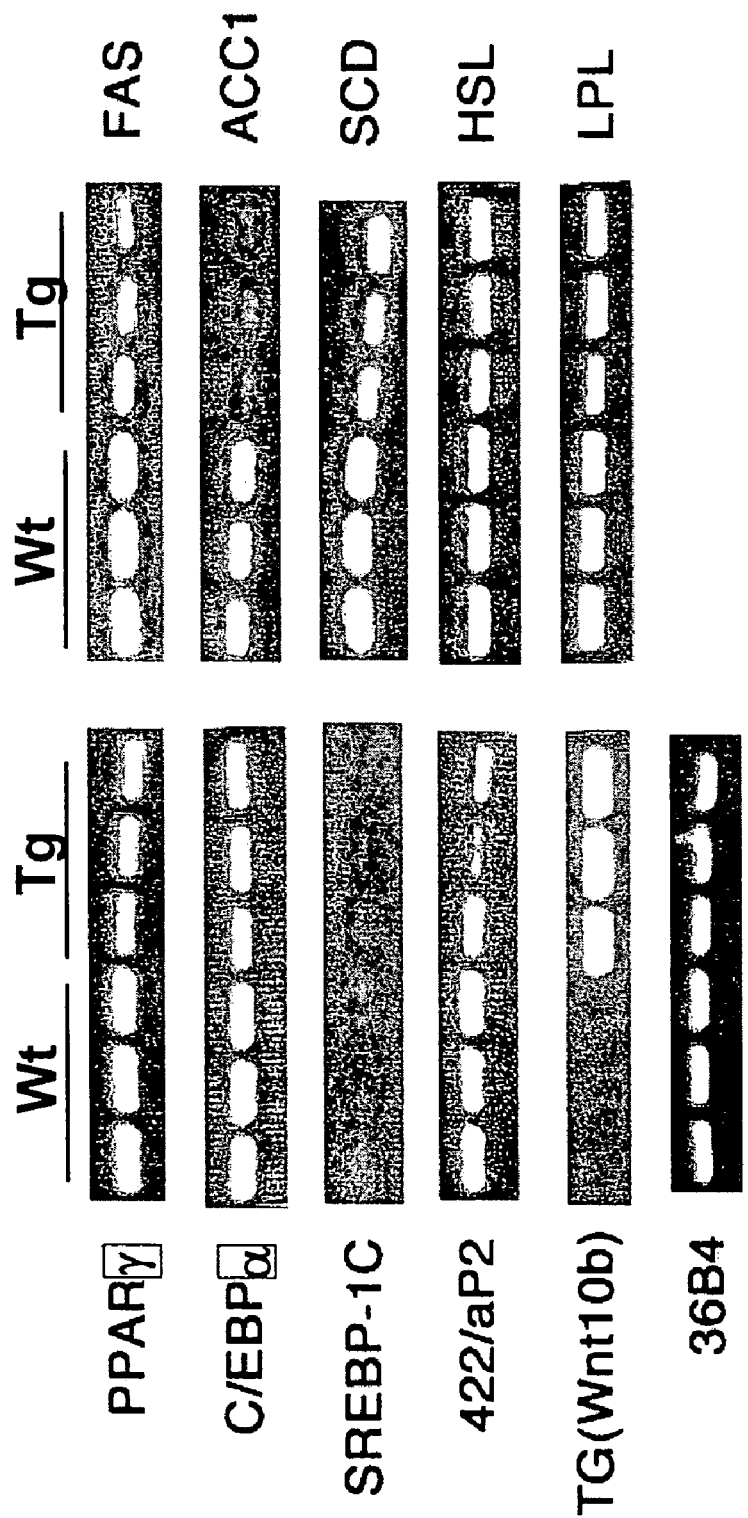
FIG. 8 shows the effect of Wnt10b on expression of adipocytes genes.

The expression of adipocytes genes was not found to be significantly altered in the Wnt10b transgenic animals (FIG. 8). Transgenic mice were found to exhibit altered respiratory quotients relative to wt mice (FIG. 9), indicating that Wnt10b transgenic mice do not store, mobilize, and metabolize fat as dynamically as wild type littermates. The transgenic mice do not exhibit hepatic steatosis.

Figure 10:
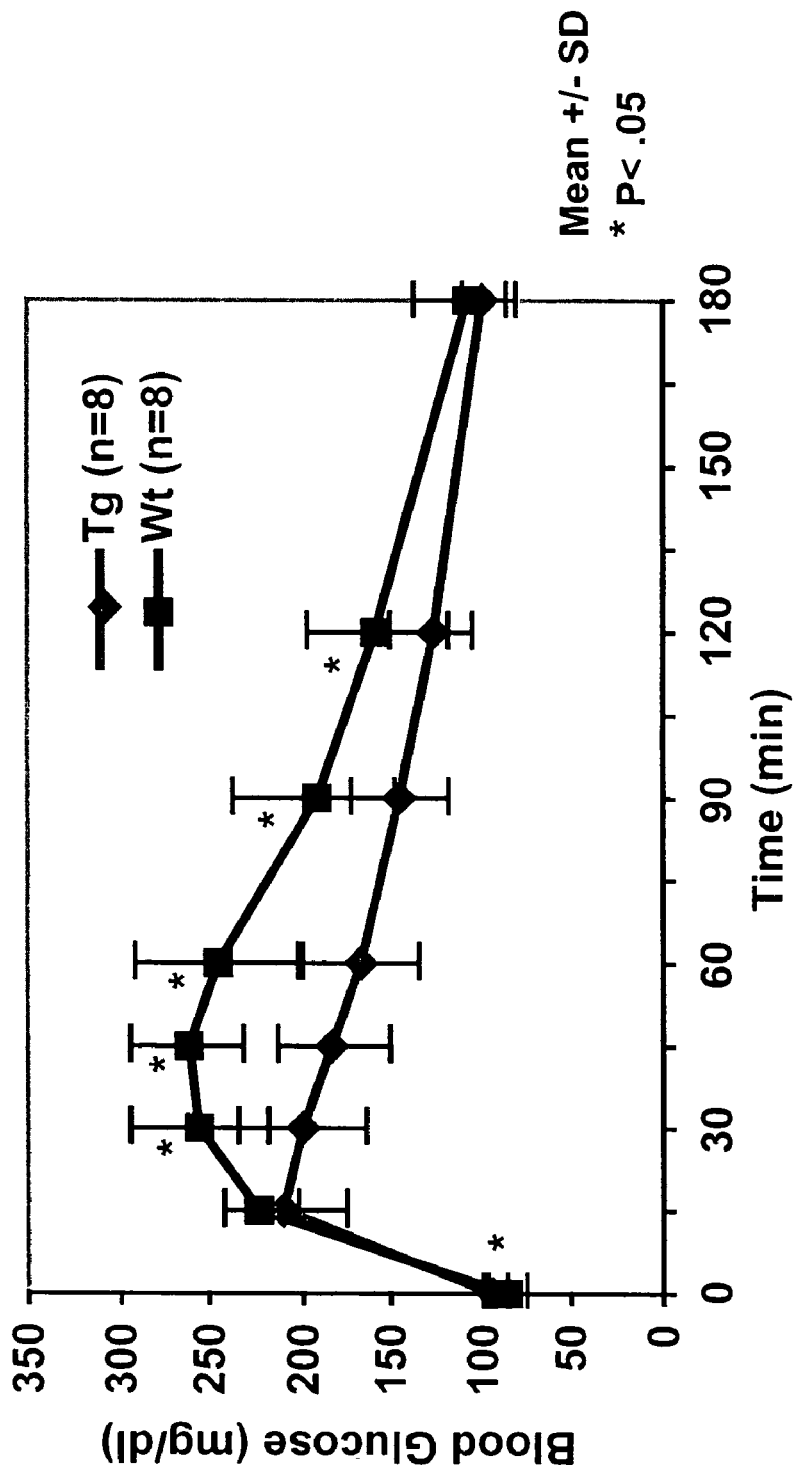
FIG. 10 shows that Wnt10b mice exhibit increased glucose tolerance.
Figure 11:
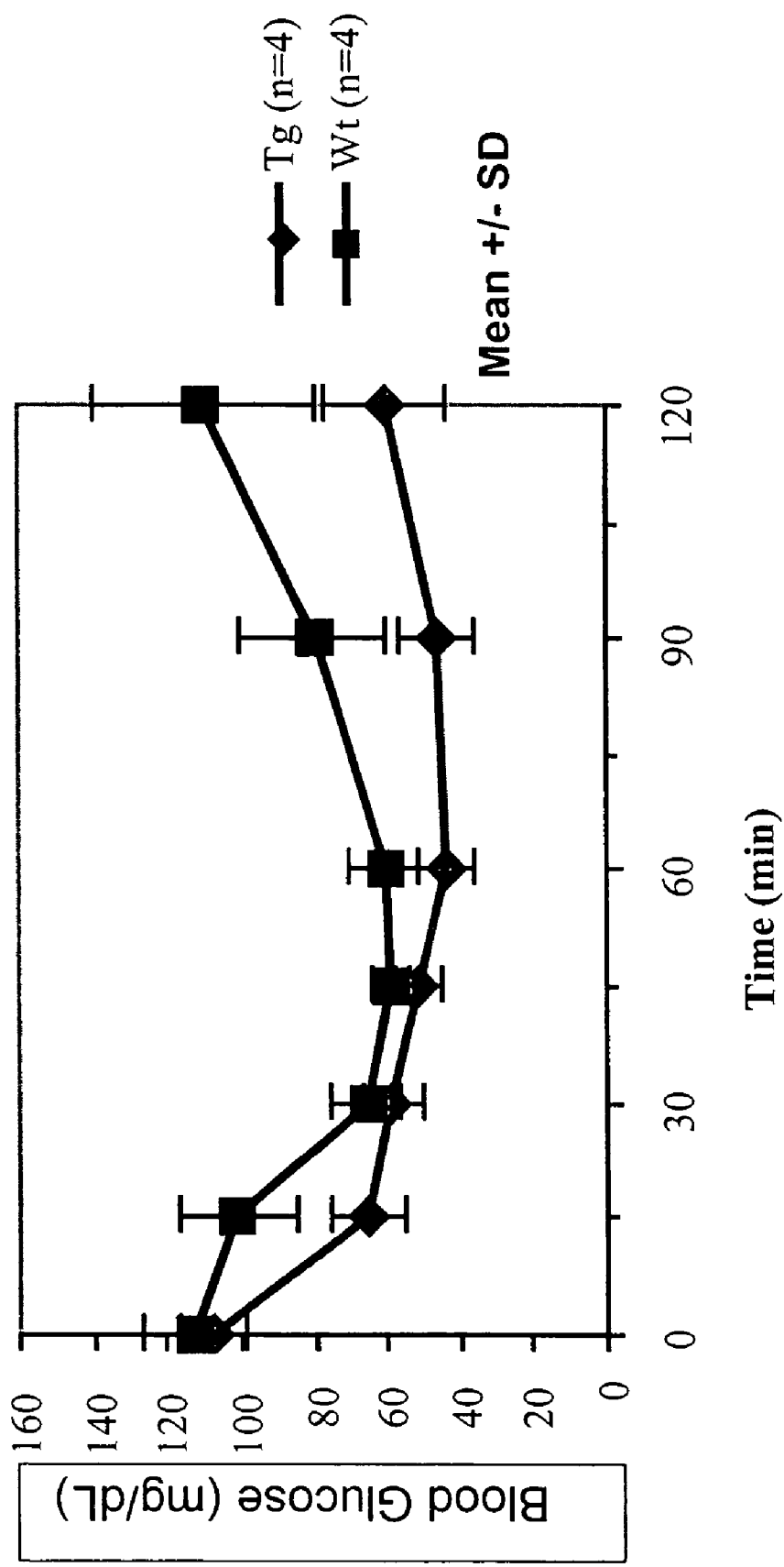
FIG. 11 shows that Wnt10b transgenic mice are more sensitive to insulin.

The Wnt10b transgenic mice were found to exhibit altered glucose metabolism relative to mice with lipodystrophy. The transgenic mice were found to be more glucose tolerant (FIG. 10) and more sensitive to insulin (FIG. 11).

Figure 2:
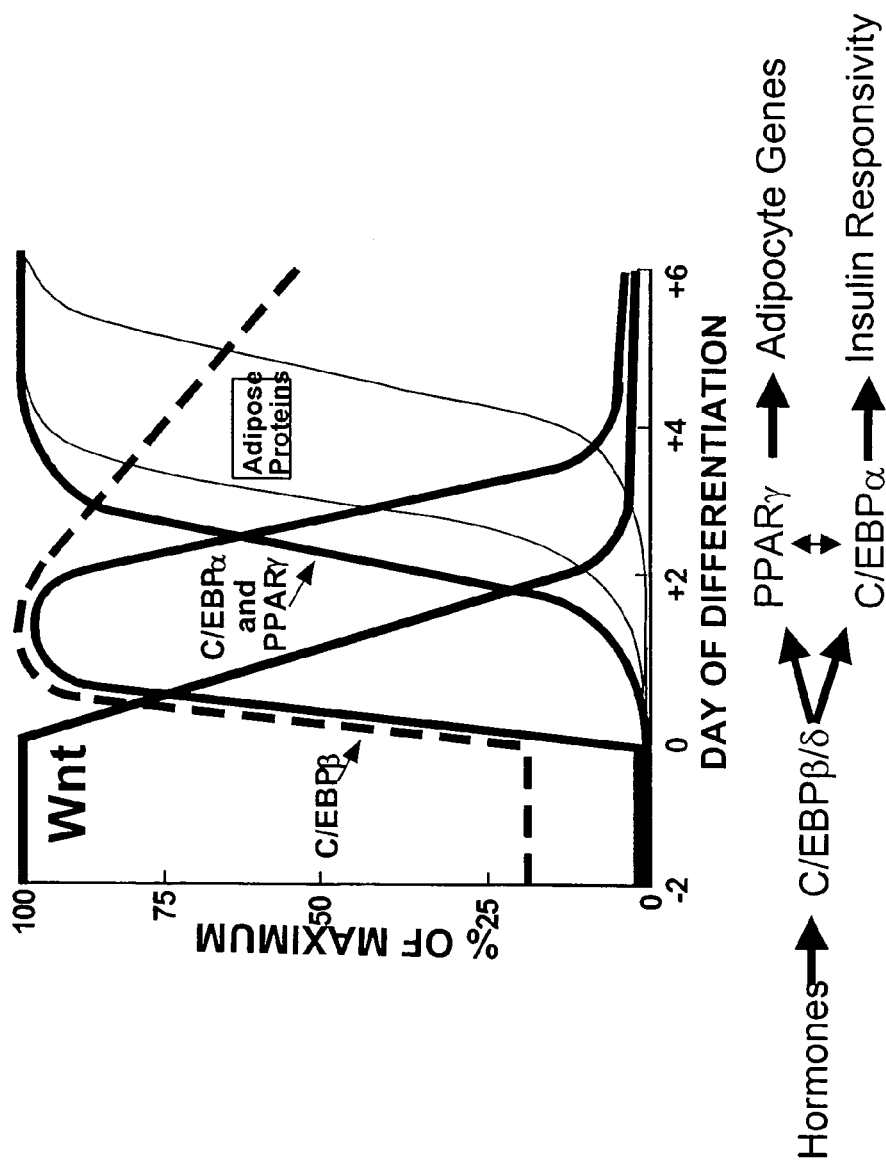
FIG. 2 shows a model of Wnt signaling in adipogenesis.

Wnt10b transgenic mice were found to exhibit altered differentiation of muscle differentiation, with preferential differentiation into the muscle lineage vs. adipocytes lineage. FIG. 2 summarizes the role of Wnt signaling in adipogenesis.

Accordingly, in some embodiments, the present invention provides animal models of Wnt10b overexpression. In other embodiments, the present invention provides animal models comprising Wnt10b knockouts or loss of function variants (See e.g., Example 2). Such knockout animals may be generated using any suitable method. The animal may be heterozygous or, more preferably, homozygous for the Wnt10b gene disruption. In some embodiments, the gene disruption comprises a deletion of all or a portion of the Wnt10b gene. In other embodiments, the gene disruption comprises an insertion or other mutation of the Wnt10b gene. In still other embodiments, the gene disruption is a genetic alteration that prevents expression, processing, or translation of the Wnt10b gene. In one embodiment, both Wnt10b gene alleles are functionally disrupted such that expression of the Wnt10b gene product is substantially reduced or absent in cells of the animal. The term "substantially reduced or absent" is intended to mean that essentially undetectable amounts of normal Wnt10b gene product are produced in cells of the animal. This type of mutation is also referred to as a "null mutation" and an animal carrying such a null mutation is also referred to as a "knockout animal." In preferred embodiments, the transgenic animals display a disease phenotype (e.g., excess fat accumulation) similar to that observed in humans.

In view of the observed phenotypes, the transgenic animals of the present invention find use for understanding and characterizing a number of diseases, conditions, and biological processes, including, but not limited to, diabetes, obesity, stroke, and coronary artery disease. A number of general screening utilities are provided below.

The present invention is not limited to a particular animal. A variety of human and non-human animals are contemplated. For example, in some embodiments, rodents (e.g., mice or rats) or primates are provided as animal models for alterations in fat metabolism and screening of compounds (See below description).

In other embodiments, the present invention provides commercially useful transgenic animals (e.g., livestock animals such as pigs, cows, or sheep) overexpressing Wnt10b. It is contemplated that meat from such animals will have desirable properties such as lower fat content and higher muscle content. Any suitable technique for generating transgenic livestock may be utilized. In some preferred embodiments, retroviral vector infection is utilized (See e.g., U.S.

Pat. No. 6,080,912 and WO/0030437; each of which is herein incorporated by reference in its entirety).

In still further embodiments, the present invention provides skin substitutes comprising altered (e.g., increased) Wnt10b expression. Experiments conducted during the course of development of the present invention demonstrated that transgenic mice overexpressing Wnt10b exhibit decreased subcutaneous fat, elevated subcutaneous collagen and increased mast cells. While not being limited to a particular mechanism, it is contemplated that skin substitutes comprising such properties find use as artificial skin for wounds and burns.

III. Applications

The transgenic animals of the present invention find use in a variety of applications, including, but not limited to, those described herein.

Utilizing Transgenic Animals for Genetic Screens

In some embodiments, the Wnt10b transgenic animals of the present invention are crossed with other transgenic models or other stains of animals to generate F1 hybrids for additional disease models. In another embodiment, a disease condition is induced by breeding an animal of the invention with another animal genetically prone to a particular disease. For example, in some embodiments, Wnt10b transgenic animals are crossed with animal models of other genes associated with obesity or related conditions.

In some embodiments, the Wnt10b animals are used to generate animals with an active Wnt10b gene from another species (a "heterologous" Wnt10b gene). In preferred embodiments, the gene from another species is a human gene. In some embodiments, the human gene is transiently expressed. In other embodiments, the human gene is stably expressed. Such animals find use to identify agents that inhibit or enhance human Wnt10b activity in vivo. For example, a stimulus that induces production of Wnt10b or enhances Wnt10b signaling is administered to the animal in the presence and absence of an agent to be tested and the response in the animal is measured. An agent that inhibits human Wnt10b in vivo is identified based upon a decreased response in the presence of the agent compared to the response in the absence of the agent.

Drug Screening

The present invention provides methods and compositions for using transgenic animals as a target for screening drugs that can alter, for example, interaction between Wnt10b and binding partners (e.g., those identified using the above methods) or enhance or inhibit the activity of Wnt10b or its signaling pathway. Drugs or other agents (e.g., from compound libraries) are exposed to the transgenic animal model and changes in phenotypes or biological markers are observed or identified. For example, in some embodiments, drug candidates are tested for the ability to alter glucose metabolism, fat storage, bone density, muscle density, adipocytes or muscle gene expression, skin properties (e.g., subcutaneous fat levels, subcutaneous collagen, and subcutaneous mast cells), and cold sensitivity in Wnt10b knockout or overexpressing animals.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., J. Med. Chem. 37: 2678–85 [1994])); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening.

Therapeutic Agents

The present invention further provides agents identified by the above-described screening assays. Accordingly, it is within the scope of this invention to further use an agent identified as described herein (e.g., Wnt10b overexpressing transgenic animal, Wnt10b transgenic knockout animal, hybrid of a Wnt10b transgenic knockout animal, progeny of Wnt10b transgenic knockout animal, neuronal modulating agent or Wnt10b mimetic, a Wnt10b inhibitor, a Wnt10b specific antibody, or a Wnt10b-binding partner) in an appropriate animal model (such as those described herein) to determine the efficacy, toxicity, side effects, or mechanism of action, of treatment with such an agent. Furthermore, agents identified by the above-described screening assays can be used for treatments of obesity related disease (e.g., including, but not limited to, diabetes and coronary artery disease).

Experimental

The following examples are provided in order to demonstrate and further illustrate certain preferred embodiments and aspects of the present invention and are not to be construed as limiting the scope thereof.

EXAMPLE 1

Wnt10b Overexpression Mouse

This example describes the generation and characterization of a Wnt10b overexpressing mouse.

A. Methods

Figure 12:
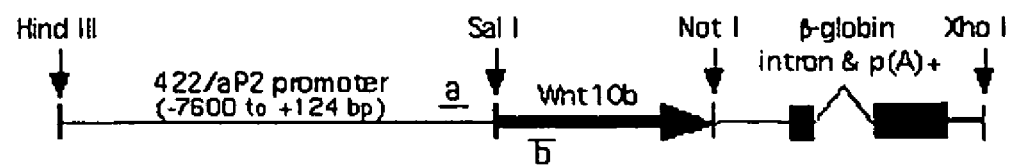
FIG. 12 shows the construct used in generating the Wnt10b overexpression mouse.

Design and creation of transgenic mice in which Wnt-10b is expressed from the adipocyte-specific 422/aP2 promoter. Transgenic mice were generated in which expression of mouse Wnt-10b is driven by the adipocyte-specific promoter from the adipocyte fatty acid binding protein, 422/aP2 (FIG. 12). This promoter has been used extensively in transgenic mouse studies and is almost exclusively expressed in white adipocytes, although expression in macrophages occurs in some cases. The 422/aP2 promoter and enhancer sequence were obtained from Dr. S. D. Clarke (University of Texas). Mouse Wnt10b was amplified using PCR and cloned. This clone was sequenced to make sure mutations were not introduced. To ensure that the Wnt10b mRNA was stable in vivo, the β-globin intron and 3' untranslated region were included. Prior to creation of transgenic mice, this construct was transiently transfected into preadipocytes, and expression of Wnt-10b confirmed. Moreover, the Wnt-10b gene was excised and cloned into a retroviral construct to prove that this construct efficiently blocked adipogenesis. Non-tagged mouse Wnt10b was used because previous efforts to create Wnt10b chimeras with HA-tag resulted in biologically inactive proteins.

Screening of Transgenic Animals. The purified transgene was injected into fertilized eggs, which were then implanted into pseudopregnant mice by the Transgenic Core facility at the University of Michigan. Pups (92 total) were delivered ~21 days later, and left in the care of the mother for an additional 21 days. Tail biopsies were performed on DNA from pieces of tail removed from pups at 14 days of age, and seven animals positive for the transgene were identified by PCR. Briefly, primers synthesized to the 5' untranslated region of the 422/aP2 gene (sense direction) and to the Wnt-10b gene (antisense direction) were used to amplify a 400 bp fragment from the 422/aP2-Wnt-10b transgene. Standard primers for the endogenous β-globin gene were used as a positive control for PCR.

Development of subcutaneous WAT. Skin samples from 7 wk old female wild type and transgenic mice were fixed with 10% buffered formalin, embedded in paraffin, sectioned (20 µM), and stained with hematoxylin and eosin.

Expression of Wnt-10b inhibits formation of brown adipocytes in interscapular BAT and in embryonic fibroblasts. Mouse pups (72 h) were dissected and fixed in 10% buffered formalin. After embedding in paraffin, samples were sectioned (20 µM), and stained with hematoxylin and eosin. Wild type BAT appears dark in color, reflecting its high mitochondrial content, with individual brown adipocytes containing the expected multilocular arrangement of lipid droplets. Transgenic BAT appears light in color, reflecting its high lipid content. At higher magnification the cells show a unilocular lipid droplet, reminiscent of white adipocytes.

Expression of molecular markers in BAT from control and transgenic mice. Interscapular BAT from seven littermates was dissected and subjected to immunoblot analyses. Expression of key markers of BAT (UCP 1, 422/aP2, and C/EBPα) was either reduced or missing in transgenic animals, while PPARγ was slightly elevated.

Wnt signaling inhibits brown adipogenesis in cultured Rb−/− mouse embryonic fibroblasts. To test the effect of Wnt in vitro, Rb −/− MEFs that express UCP-1 when induced to differentiate were used. The early and sustained application of lithium, which mimics Wnt signaling by inhibiting GSK3, completely blocked UCP-1 expression in differentiating Rb −/− MEFs, and reduced expression of adipogenic markers C/EBPα, 422/aP2, and to a lesser extent, PPARγ.

Expression of Wnt-10b inhibits the dynamic use of fatty acids as an energy source. Indirect calorimetry was performed on wild type (n=4) and transgenic (n=4) animals maintained on Rodent Diet 5001 (PMI Nutrition International), with 12.1% of calories from fat. Oxygen consumption (VO2, ml/kg/hr) and carbon dioxide production (VCO2, ml/kg/hr) were determined using the Oxymax2000 (Columbus Instruments), and were used to calculate respiratory quotient (RQ; VCO2/VO2) as a measure of metabolic efficiency. Differences between wild type and transgenic rates were statistically different in both dark and light cycles ($P<0.05$).

B. Results

Of the eight transgenic founders, two females and one male have a defect in development of BAT and WAT. While the two female founders were fertile, they did not suckle their young because of impaired mammary gland development. Thus, surrogate mothers were used to rescue their progeny. Male progeny were obtained for use in propagating both these lines. While the phenotype appears similar in lines from the three independent founders, preliminary data reported herein is from progeny of the male transgenic founder. The other five founders were not pursued as one was growth retarded and infertile, two did not transmit the transgene to progeny and two showed no evidence of phenotype.

The transgene was expressed in both white adipose tissue (WAT) and brown adipose tissue (BAT) (FIG. 3). The transgenics were lighter in weight at 3 weeks of age but heavier at 5 weeks of age.

The transgenic mice exhibited altered bone trabecular thickness and spacing (FIG. 4). Microcomputerized tomography on femurs of mice at six months of age revealed that although cortical bone was not greatly affected by expression of Wnt10b, trabecular bone as a fraction of total bone volume increased ~4 fold. This was as a result of increased thickness and number of trabeculi.

To assess whether increased femoral trabeculation enhances bone strength, material properties of bones from control and FABP4-Wnt10b mice were examined. Mechanical testing by four point bending indicated that femurs from FABP4-Wnt10b mice have increased ultimate load and stiffness compared to wild type littermates. In contrast, no differences were observed in other mechanical properties including yield load, energy (Nmm), or displacement ratio. Thus, Wnt10b signaling increases bone mass, which in turn increases bending and strength without adversely impacting bone material properties.

To determine whether Wnt10b influences the loss of bone with aging, bones from wild type and FABP4-Wnt10b mice at 23 months of age were analyzed by mCT. While aged wild type mice have less trabecular bone than young mice, FABP4-Wnt10b mice retain extensive trabeculation throughout the entire endocortical compartment. Quantification of a 1 $mm^3$ region of trabecular bone in distal femur indicated that bone volume fraction is statistically increased from 2.6% in wild type mice to 34% in FABP4-Wnt10b mice ($P<0.01$), with comparable increases in bone mineral density (100 vs 424 mg/cc; $P<0.01$). As observed in younger mice, aged FABP4-Wnt10b mice have more trabeculi than wild type mice (5.2 vs. 0.57; P<0.001), with a concomitant decrease in trabecular spacing (0.15 vs. 5.7 mm; P<0.05). No differences were observed in thickness of trabeculi. Histological analysis further supports the observation that aged FABP4-Wnt10b mice have a dramatic increase in trabeculation of distal femur compared to wild type controls. Thus, FABP4-Wnt10b mice appear to accrue trabecular bone throughout life, and resist bone loss associated with aging.

Expression of Wnt10b in adipocyte precursors or developing adipocytes within marrow influences the development of mesenchymal stem cells. Adipocytes and osteoblasts are derived from a common pool of precursor cells (mesenchymal stem cells). The present invention is not limited to a particular mechanism. Indeed, an understanding of the mechanism is not necessary to practice the present invention. Nonetheless, it is contemplated that the increase in trabeculi may be because inhibition of adipogenesis by Wnt10b increases the precursor pool available for osteoblastogenesis. In addition, osteoblastogenesis may be directly stimulated by local production of Wnt10b. LRP5 is a Wnt coreceptor and LRP5 −/− mice have reduced bone density (osteoporosis; Kato et al., J Cell Biol 2002, 157: 303–14). Thus, the transgenic animals of the present invention represent the gain of function animal model in which increased Wnt signaling results in increased bone formation.

FIG. 5 demonstrates that Wnt10b overexpression in the transgenics blocks expression of adipocyte genes in newborn mice and adult mice (FIG. 6). The transgenic mice were also found to be cold sensitive (FIG. 7). The transgenic mice were further found to exhibit decreased levels of subcutaneous fat, elevated subcutaneous collagen and increased mast cells.

The present invention is not limited to a particular mechanism. Indeed, an understanding of the mechanism in not necessary to practice the present invention. Nonetheless, it is contemplated that, although expression of some adipocyte genes was not found to be altered in fat from Wnt10b transgenic animals (FIG. 8), the decreased expression of SREBP1c and its downstream genes may indicate that the capacity for de novo fatty acid synthesis is reduced in transgenic mice. Moreover, the increased glucose tolerance and insulin sensitivity described below may be because Wnt10b acts on fully-differentiated adipocytes to alter expression/secretion of adipocyte hormones (e.g. leptin, ACRP30, resistin), which are well known to influence whole body insulin action. Alternatively, Wnt10b may act through an unknown mechanism to influence whole body glucose metabolism.

Transgenic mice were found to exhibit altered respiratory quotients relative to wt mice (FIG. 9), indicating that Wnt10b transgenic mice do not store, mobilize, and metabolize fat as dynamically as wild type littermates. The transgenic mice do not accumulate lipid in liver, muscle or pancreatic β-cells.

The Wnt10b transgenic mice were found to exhibit altered glucose metabolism relative to mice with lipodystrophy. The transgenic mice were found to be more glucose tolerant (FIG. 10) and more sensitive to insulin (FIG. 11). Briefly, male mice at eight weeks of age were fasted overnight and injected intraperitoneally with glucose or insulin. Concentration of blood glucose was then monitored over time to determine the ability of control and transgenic mice to metabolize glucose (FIG. 10), or respond to insulin (FIG. 11). Similar results were observed with female mice.

Wnt10b transgenic mice were found to exhibit altered differentiation of muscle differentiation, with preferential differentiation into the muscle lineage vs. adipocytes lineage. FIG. 2 summarizes the role of Wnt signaling in adipogenesis.

Adipocyte-specific expression of Wnt10b inhibits formation of WAT. To determine if expression of Wnt10b from the 422/aP2 promoter inhibits the earliest development of WAT, transgenic and wild type pups were sacrificed 72 h after parturition. Although mice are not normally born with white adipocytes, they develop rapidly over the first few days, with the inguinal site being the first to develop. After fixing, sectioning and staining, the inguinal and subcutaneous depots appeared similar between genotypes, consistent with the 422/aP2 promoter activating expression of Wnt10b too late to inhibit this first wave to adipocyte formation. When two wild type and two transgenic females were sacrificed at 7 wks of age, the ovarian fat pad was diminished by 85% in Wnt10b transgenic mice, although fat size and morphology appeared similar in the adipocytes that did develop. This decrease in WAT was not restricted to the perigonadal depot, as histological analysis revealed that transgenic animals had greatly reduced numbers of adipocytes in all central and peripheral fat depots. Further histological analysis revealed that the subcutaneous fat depot was reduced even more substantially than other sites. Although the dermis, hair follicles, muscle and glandular structures appeared unaltered by the transgene, the formation of fat within this depot was almost completely inhibited. This is consistent with the 422/aP2 promoter having higher levels of activity within subcutaneous adipocytes than in other perigonadal sites. These data are consistent with Wnt10b being a potent inhibitor of WAT development.

Expression of Wnt10b inhibits formation of BAT. Brown adipogenesis has many similarities to white adipogenesis, including important roles for the adipogenic transcription factors C/EBPα and PPARγ. Since Wnt signaling completely inhibits induction of C/EBPα and PPARγ during differentiation of 3T3-L1 preadipocytes, and since the 422/aP2 promoter is expressed in brown adipocytes, it was examined whether Wnt10b inhibited BAT development. In wild type mice, BAT is first observed late during gestation and the largest and most easily recognizable depot of BAT is interscapular. Although smaller depots of BAT are associated with most organs (e.g., thymus, kidney, spleen) and tissues (e.g., muscle), this BAT is usually interspersed within WAT. Transgenic mice that express Wnt10b from the 422/aP2 promoter did not develop interscapular BAT at 72 h. Histological analyses did not reveal BAT depots elsewhere in the body. While the tissue that developed in place of interscapular BAT had the morphological appearance of white adipose tissue, the lipid filled cells do not have characteristics of either mature white or brown adipocytes. For example, interscapular tissue from Wnt10b transgenic mice does not express UCP1, a key protein for brown adipocyte thermogenesis, C/EBPα, which is required for adipogenesis and the acquisition of insulin sensitivity, or 422/aP2, the adipocyte lipid binding protein and a marker of the fully differentiated adipocyte phenotype (FIG. 15A). In contrast, the interscapular tissue does express PPARγ, suggesting that Wnt10b specifically blocks the ability of this adipogenic transcription factor to activate expression of its downstream targets, UCP1, C/EBPα, and 422/aP2. These data suggest that Wnt10b inhibits formation of brown adipogenesis during development of BAT.

Figure 14:
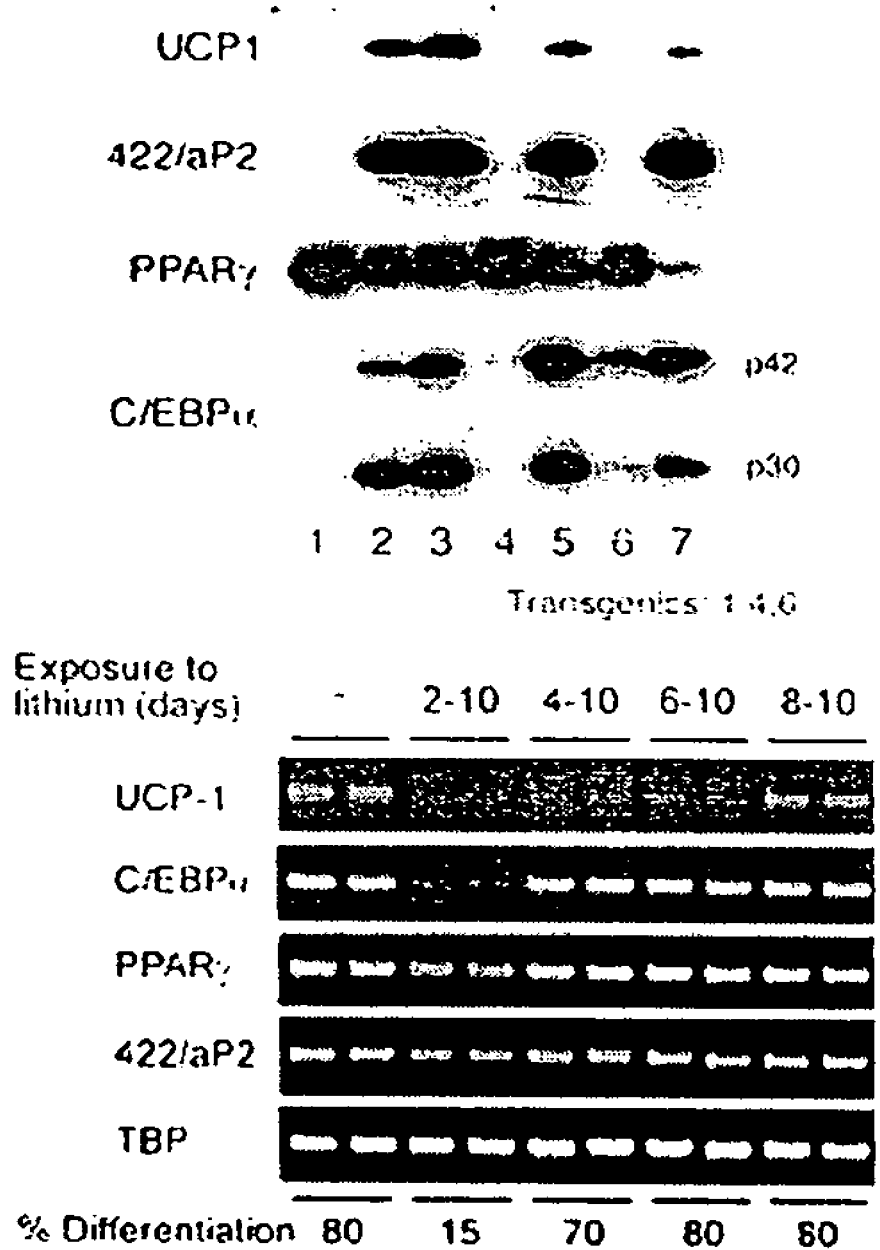
FIG. 14 shows the effect of Wnt signaling on differentiation of a brown adipocytes cell culture model.

Wnt Signaling Inhibits Brown Adipogenesis in Cultured Cells. Progress to understand brown adipogenesis has been hindered by the lack of a good cell culture model. Although a number of brown preadipocyte lines have been developed, these lines do not have mitochondriogenesis or levels of UCP1 expression comparable to that in BAT. To determine if Wnt signaling inhibits differentiation of this brown adipocyte model, the Wnt pathway was activated with lithium at various times during the process of brown adipogenesis, and rtPCR was used to assess expression of brown adipocyte genes. In this preliminary experiment, treatment with lithium starting at day two (2–10) largely blocked differentiation as assessed by the proportion of cells that accumulated lipid droplets by day 10 (15% vs. 80%; FIG. 14B). This inhibition of differentiation was associated with an almost complete block in the induction of UCP-1, C/EBPα and 422/aP2, with lesser suppression observed for PPARγ. Exposure to lithium later during brown adipogenesis (e.g. day 6–10) did not block the proportion of cells that accumulated lipid droplets; however, active Wnt signaling still potently suppressed expression of UCP-1 (FIG. 14B), similar to the inhibition of UCP1 by Wnt10b observed during development of BAT in Wnt10b transgenic mice (FIG. 14A). Thus, these cells provide an in vitro model that recapitulates many of the essential aspects of effects of Wnt10b on development of BAT.

Figure 9:
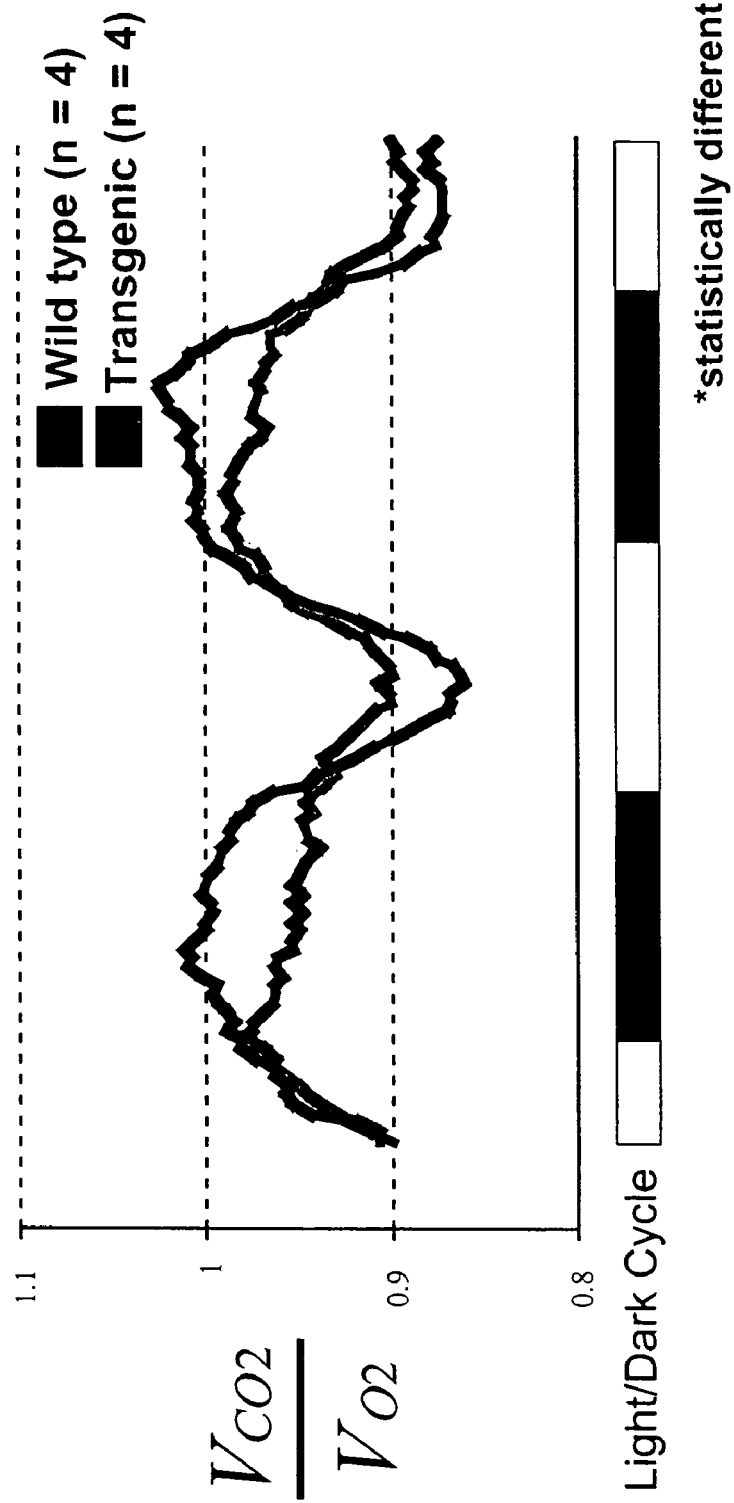
FIG. 9 shows the respiratory quotients of control and Wnt10b transgenic mice.

Transgenic animals deficient in WAT and BAT have an inability to store and mobilize fat. Inhibition of WAT and BAT development by Wnt10b is likely to have profound physiological consequences. For example, WAT is the site for storage of energy after a meal and release of energy during the postabsorptive state. To determine the effect of Wnt10b on the ability of transgenic mice to utilize fatty acids for energy, respiratory quotient in control and Wnt10b animals over a 48 h period was measured (FIG. 9). During the night, when wild type mice were eating and active, they selectively used carbohydrate for their energy source, storing dietary and hepatic fatty acids for later (respiratory quotient approaching 1). During the day when these mice were sleeping and eating less, they mobilized their stored fat reserves, and increased the proportion of fatty acids oxidized as a fuel source (respiratory quotient approaching 0.7). In contrast, Wnt10b transgenic mice oxidized as their fuel source a higher proportion of fatty acids at night and a lower proportion of fatty acids during the day. These data indicate that Wnt10b transgenic mice have an impaired ability to store and mobilize fatty acids.

In wild type animals, a higher VCO2/VO2 ratio during the dark cycles (active feeding phase) demonstrates reliance on carbohydrate as a source of fuel. During light cycles (sleep and fasting phase), animals derive more of their energy from fatty acid oxidation, which is reflected as a lower VCO2/VO2 ratio. Metabolic efficiency of transgenic animals oscillates in a more narrow range, which may be explained by their inability to store fat while feeding and thus utilize fatty acids for fuel during the dark cycle as a result of effects of elevated blood lipid.

Effect of Wnt10b on Development of Obesity

To ascertain whether Wnt10b inhibits development of genetic obesity, mice that have a naturally occurring mutation in the agouti gene ($A^y$) were crossed with FABP4-Wnt10b mice. Mutation of agouti causes obesity due to hyperphagia and reduced energy expenditure (Wolff, J. Nutr. 127:1897S 1997). At 16 weeks of age, body composition of agouti mice is ~50% fat. However, agouti mice that carry the FABP4-Wnt10b transgene remain lean, with ~22% body fat. While obese agouti mice show evidence of type II diabetes, expression of the Wnt10b transgene normalizes glucose tolerance of these mice. Thus, Wnt10b inhibits accumulation of white adipose tissue in a genetic model of obesity, with corresponding improvements in glucose tolerance.

EXAMPLE 2

Wnt10b Knockout Mouse

Figure 13:
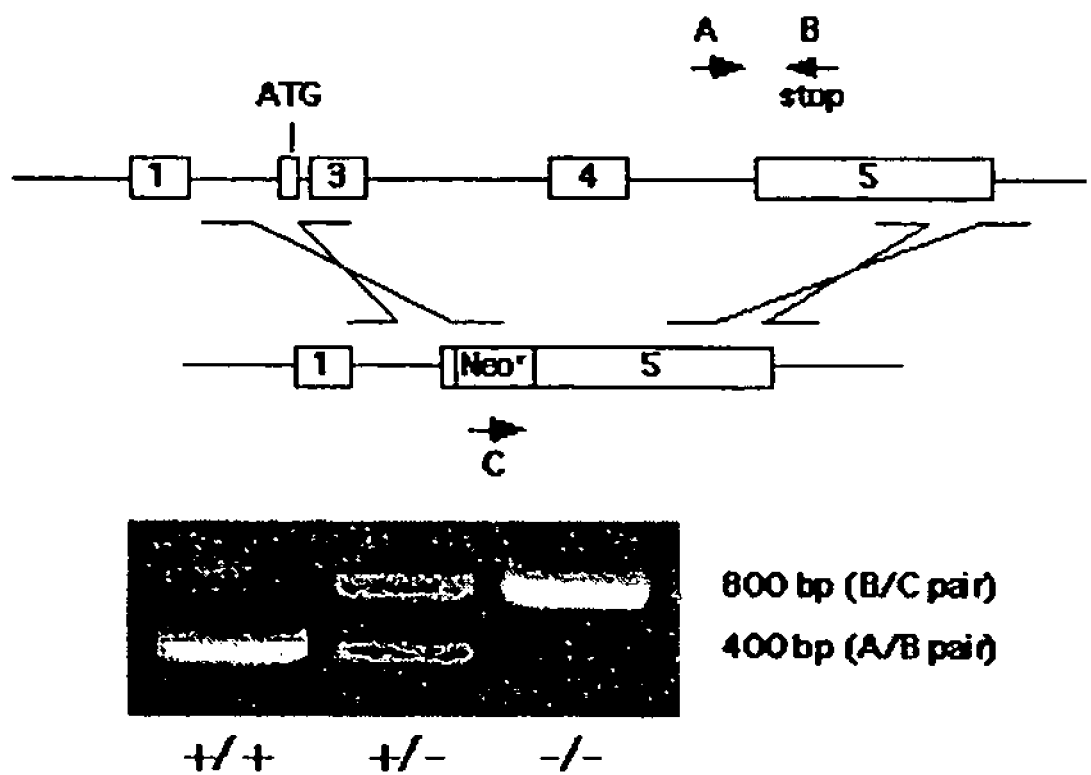
FIG. 13 shows the construct used in generating the Wnt10b null mouse.

This Example describes the creation and initial characterization of mice deficient for Wnt-10b. FVB mice, in which the Wnt10b locus is disrupted, were received from Dr. Timothy Lane (UCLA) and Dr. Philip Leder (Harvard University). The strategy used to disrupt the Wnt10b gene and the PCR-based screening strategy is shown in FIG. 13. Preliminary observations are that mice deficient in Wnt-10b are viable and reproductively competent. Gross morphology does not reveal an obvious defect in externally observed traits such as growth, hair or skin development, or behavior.

In vitro data indicate that inhibition of Wnt signaling in myoblasts results in a loss of commitment to the muscle lineage, and a redirecting of differentiation to the adipocyte phenotype. Experiments in Wnt10b –/– mice support these in vitro findings. After consumption of a high fat diet and cold-injury of leg muscle, myoblasts in control animals rapidly proliferate and differentiate to regenerate the injured muscle within 1 week. In contrast, differentiating myoblasts in Wnt10b –/– mice accumulate lipid and express adipocyte markers. Thus, a loss of Wnt10b may play a key role in the increased adipocyte formation within muscle, and overall decreased muscle mass, with aging. Moreover, direct effects of Wnt10b on muscle metabolism may contribute to the altered glucose metabolism and insulin sensitivity described in FIGS. 10 and 11.

These animals are used to test the hypothesis that Wnt10b acts to restrain development of adipocytes within adipose tissue. Given the paracrine actions of Wnt10b and the central role of preadipocytes not only in adipose tissue, but also in marrow and muscle, development of blood cells, bone, and muscle are evaluated. Experiments are designed to investigate whether Wnt10b –/– mice are predisposed to obesity under dietary or genetic conditions that lead to increased WAT accumulation. In addition, experiments are used to determine if a deficiency of Wnt10b allows cultured MEFs to spontaneously differentiate into adipocytes in the absence of standard inducing agents. These animals further serve as animal models for screening for pharmaceuticals.

EXAMPLE 3

Decreased Bone Mass in Wnt10b –/– Mice.

To determine whether signaling by endogenous Wnt10b regulates bone mass, mice with a deletion of the Wnt10b open reading frame were generated. Analysis with mCT revealed that bone volume fraction in distal metaphyseal femur is decreased by 30% in Wnt10b –/– mice with a comparable decline in bone mineral density. Decreased bone volume fraction is due to a decrease in trabecular number. While no change is observed in trabecular thickness, there is a corresponding increase in trabecular spacing. Quantitative analyses of wild type and Wnt10b –/– femora by histomorphometry provide independent support for these observations. In addition to decreased bone mass in femur, Wnt10b –/– mice also have decreased bone volume fraction in proximal tibia. The present invention is not limited to a particular mechanism. Indeed, an understanding of the mechanism is not necessary to understand the present invention. Nonetheless, it is contemplated that the comparable reduction in bone volume fraction and other bone variables in Wnt10b −/− and LRP5 −/− mice suggests that the bone phenotype in LRP5 −/− mice may reflect a loss of endogenous Wnt10b signaling. Decreased serum osteocalcin and unaltered serum TRAP5C activity in Wnt10b. −/− mice suggests that the decrease in trabecular bone arises due to a decrease in bone formation rather than an increase in resorption. Although results in mesenchymal precursors suggest an effect of Wnt signaling on osteoblast differentiation, the mechanism could also involve osteoblast proliferation, function, or turnover. Effects of Wnt10b appear to be independent of leptin since wild type and Wnt10b −/− mice have similar serum concentrations of this hormone. Thus, results from Wnt10b transgenic and null mice provide compelling evidence that Wnt10b regulates trabecular bone mass.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A transgenic mouse whose genome comprises a heterologous nucleic acid sequence comprising a nucleic acid sequence encoding mouse Wnt10b operably linked to a murine 422/aP2 promoter, wherein the adipose tissue of said transgenic mouse exhibits a higher level of Wnt10b mRNA expression than that of a mouse comprising no heterologous nucleic acid sequence, and wherein said transgenic mouse exhibits decreased subcutaneous fat, and wherein said mouse further comprises characteristics of: increased glucose tolerance, increased insulin sensitivity, increased cold sensitivity, elevated subcutaneous collagen, increased subcutaneous mast cells, and a decrease in mRNA levels of sterol regulatory element binding protein-1c (SREBP1c), 422/aP2, fatty acid synthetase (FAS), acetyl-CoA carboxylase (ACC1), and stearoly-CoA desaturase (SCD) in adipose tissue.

2. The transgenic mouse of claim 1, wherein said subcutaneous fat is white adipose tissue.

3. The transgenic mouse of claim 1, wherein said subcutaneous fat is brown adipose tissue.

* * * * *